United States Patent [19]

Aida et al.

[11] Patent Number: 5,243,985
[45] Date of Patent: Sep. 14, 1993

[54] LITHOTRITY APPARATUS HAVING A MISSED-SHOT PREVENTIVE FUNCTION

[75] Inventors: Satoshi Aida, Tokyo; Nobuyuki Iwama, Tochigi, both of Japan

[73] Assignee: Kabushiki Kaisha Toshiba, Kawasaki, Japan

[21] Appl. No.: 707,784

[22] Filed: May 30, 1991

[30] Foreign Application Priority Data

May 31, 1990 [JP] Japan .................................. 2-142002
May 31, 1990 [JP] Japan .................................. 2-142004

[51] Int. Cl.$^5$ ............................................. A61B 17/22
[52] U.S. Cl. ............................ 128/660.03; 128/24 EL
[58] Field of Search .............. 128/660.03, 24 EL, 804

[56] References Cited

U.S. PATENT DOCUMENTS

| 4,634,917 | 1/1987 | Dvorsky et al. | |
| 4,771,787 | 9/1988 | Wurster et al. | |
| 4,803,995 | 2/1989 | Ishida et al. | |
| 4,986,259 | 1/1991 | Aida et al. | 128/660.03 |
| 5,009,232 | 4/1991 | Hassler et al. | 128/24 EL |
| 5,076,277 | 12/1991 | Iwama et al. | 128/660.03 |
| 5,078,143 | 1/1992 | Okazaki et al. | 128/660.03 |

FOREIGN PATENT DOCUMENTS

| 244730 | 11/1987 | European Pat. Off. |
| 257199 | 3/1988 | European Pat. Off. |
| 2722252 | 11/1978 | Fed. Rep. of Germany |
| 2600521 | 12/1987 | France |
| 62-49843 | 3/1987 | Japan |
| 63-5736 | 1/1988 | Japan |

Primary Examiner—Ruth S. Smith
Attorney, Agent, or Firm—Oblon, Spivak, McClelland, Maier & Neustadt

[57] ABSTRACT

An electromagnetic induction type lithotrity apparatus, having a shock-wave source utilizing electromagnetic induction to generate a shock-wave, and focusing means to focus the shock-wave at a predetermined position, for focusing and irradiating the shock-wave toward a stone in the body of a patient which is located at the predetermined position, thereby pulverizing the stone. The apparatus comprising a drive section (sending section) for driving the shock-wave source by a voltage lower than that for generating the shock-wave so as to send a low-pressure wave lower in pressure than the shock-wave to the inside of the body, an echo receiving section, including a piezoelectric film arranged in front of the shock-wave source, for receiving a low-pressure echo reflected from the body, an echo detecting section for detecting the intensity of an echo, among the echoes received by the echo receiving section, reflected by a focal zone of the shock-wave, and a control section for comparing the intensity of the echo detected by the echo detecting section with a predetermined value, sending a predetermined signal to the drive section (sending section) based on the comparison result, switching the drive voltage of the shock-wave source to a high voltage sufficient for lithotrity, and generating a signal for driving the shock-wave source.

3 Claims, 6 Drawing Sheets

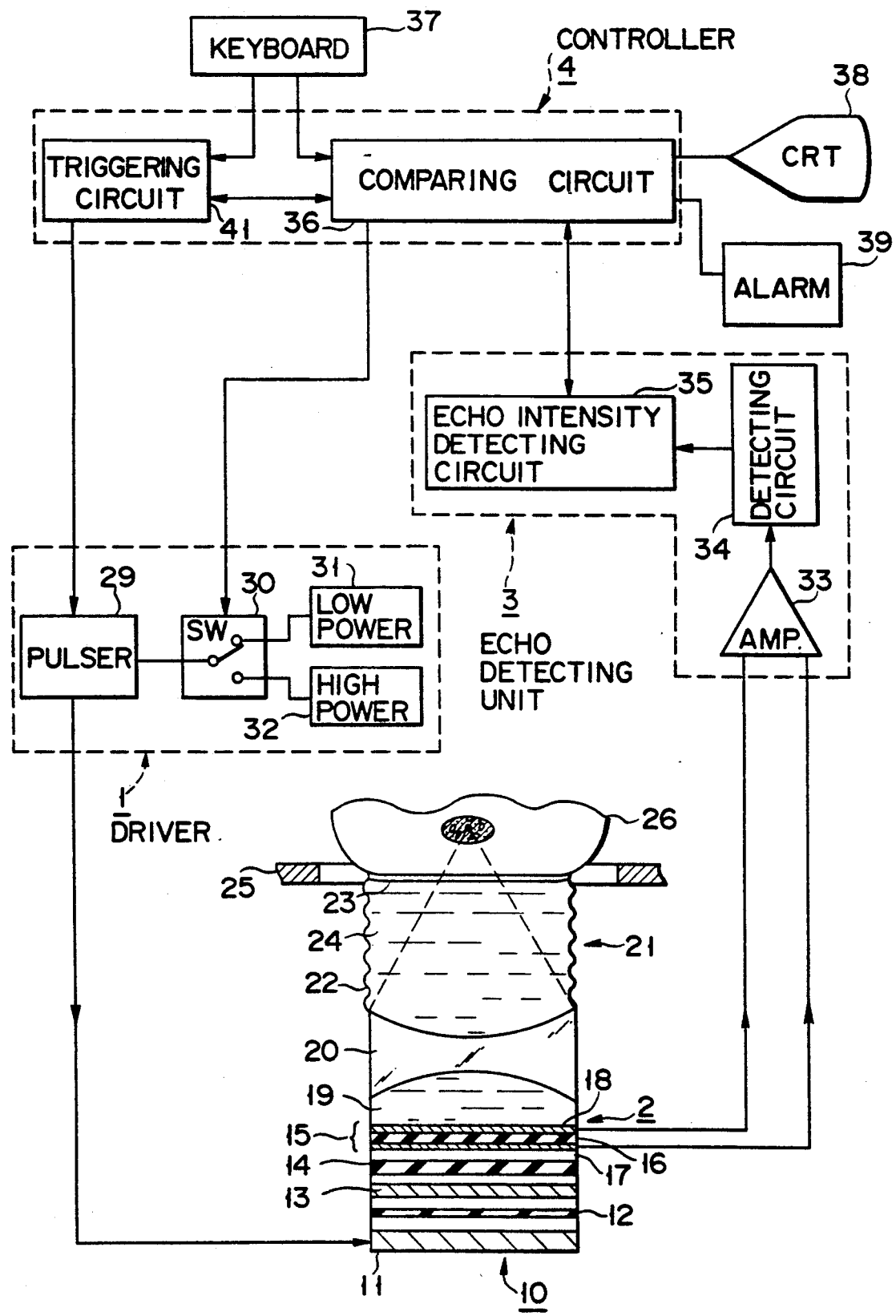
F I G. 1B

LITHOTRITY APPARATUS HAVING A MISSED-SHOT PREVENTIVE FUNCTION

BACKGROUND OF THE INVENTION

1. Field of the Invention

The present invention relates to a lithotrity apparatus utilizing an electromagnetic induction type shock-wave source, and a lithotrity apparatus utilizing an underwater discharge type shock-wave source, both of which pulverize a stone in a patient's body by irradiating the stone with a shock-wave.

2. Description of the Related Art

In a recent treatment of a stone mainly in a kidney or a gall bladder, a method of pulverizing the stone without operation for a patient's body by using a shock-wave has been widely used. As a shock-wave source an underwater discharge type, electromagnetic induction, micro explosion type, and piezoelectric type are proposed. Among them, lithotrity apparatuses of underwater type and micro explosion type have the following arrangement. A shock-wave is generated by a shock-wave source arranged at the first focal point on an ellipsoidal reflecter and is focused on the second focal point. The shock-wave irradiates a stone positioned at the second focal point.

FIG. 6 shows an applicator of a lithotrity apparatus using an electromagnetic induction type shock-wave source, which is a typical example of an electromagnetic induction type lithotrity apparatus. In an electromagnetic induction type shock-wave source 60, a flatly wound coil 61, an insulating sheet 62, and a conductive plate 63 are arranged in parallel to each other and to be extremely close to each other. The coil 61 is connected to a drive circuit (not shown). When a steep high-voltage pulse is momentarily applied to the coil 61, the coil 61 momentarily generates an intense magnetic flux. Since the magnetic flux penetrates the conductive plate 63, an eddy current is generated in the conductive plate 63 in a direction to cancel the magnetic flux. As a result, an intense repulsive force is generated between the coil 61 and the conductive plate 63 to emit an intense plane wave into water 64 contacting the conductive plate 63. The plane wave is focused on a focal point 66 by an acoustic lens 65. At this time, the pressure wave (plane wave) induces water non-linearity as it propagates in the water 64, and is then changed to a shock-wave at the focal point 66. When the position of the focal point 66 coincides with that of a stone, pulverization is performed.

This method is more advantageous than a piezoelectric type method in that a high-power output can be obtained with a comparatively small shock-wave source.

However, in a lithotrity apparatus which uses a piezoelectric as the shock-wave source, echo signals which are reflected by a focal zone can be received and derived as an electrical signal.

Published Unexamined Japanese Patent Application No. 60-191250 and Japanese Patent Application No. 61-149562 propose a lithotrity apparatus having a missed-shot preventive function. According to this apparatus, the feature of a piezoelectric type lithotrity apparatus is utilized. A piezoelectric sends a weak ultrasound immediately before an intense shock-wave is generated. When intense echoes of the ultrasound are received, it is determined that the focal point of the ultrasonic wave coincides with the stone. In this state, a shock-wave for pulverizing the stone is emitted. With this mechanism, a calculus treatment can be performed without erroneously irradiating a normal tissue other than a stone with a shock-wave. As a result, a side effect can be decreased and the pulverizing efficiency can be improved.

In addition to the lithotrity apparatus having the above-mentioned mechanism, in another lithotrity apparatus, an electromagnetic induction type shock-wave source is used, and the shock-wave source uses a rotating elliptic reflecting mirror. In the apparatus having this mechanism, it is checked by using X-rays whether a stone is aligned with the focal point. Then, a shock-wave continuously irradiates the stone while keeping synchronism with an ECG trigger. With this method, however, boresighting cannot catch up with a shift in position of the stone as the is breathing. Therefore, a shock-wave may erroneously irradiate a normal tissue other than the stone, damaging the normal tissue.

In general, an electromagnetic induction type lithotrity apparatus can generate a high-power output with a comparatively smaller shock-wave source than that of a piezoelectric type lithotrity apparatus. It is also easier to control various conditions of the shock-wave than those in an underwater discharge type lithotrity apparatus.

In the electromagnetic induction type lithotrity apparatus using the electromagnetic induction type shock-wave source described above or an underwater discharge type lithotrity apparatus, however, echoes from the inside of the patient's body cannot be received. Therefore, such an apparatus cannot incorporate a missed-shot preventive function based on detection of an echo intensity.

SUMMARY OF THE INVENTION

It is the first object of the present invention to provide, in a lithotrity apparatus using an electromagnetic induction type shock-wave source, a lithotrity apparatus having a missed-shot preventive function which can receive echoes of a low-pressure wave, reflected by the inside of a patient's body, to detect the echo intensity, and can control shock-wave radiation to an optimum state.

It is the second object of the present invention to provide, in an underwater discharge type lithotrity apparatus in which a shock-wave source is arranged at the first focal point of a rotating elliptic reflecting mirror, a lithotrity apparatus having a missed-shot preventive function which can receive echoes sent from the inside of a patient's body to detect the echo intensity, and can control shock-wave radiation to an optimum state.

It is the third object of the present invention to provide a lithotrity apparatus which detects echoes of a low-pressure wave reflected by a predetermined region and determines the echo intensity, thereby making an alarm to an operator in accordance with the situation.

In order to achieve the objects described above, the present invention is characterized in that an echo detecting sensor for detecting echoes of a shock-wave, or a low-pressure wave lower in pressure than the shock-wave, generated by a shock-wave source is provided in the vicinity of the first focal point of a rotating elliptic reflecting mirror, the intensity of each echo is detected by the sensor and thereafter is compared with a predetermined value, and radiation of a shock-wave from the shock-wave source is controlled in accordance with the comparison result. As the echo detecting sensor, a piezoelectric or a semiconductor distortion sensor is used. An ultrasonic probe for sending and receiving an ultrasonic wave can be used in place of the detecting sensor. When an ultrasonic probe is used, an ultrasonic wave may be sent/received immediately before the shock-wave source emits a shock-wave.

According to the present invention, in order to achieve the first object, the following mechanism (means) is provided. More specifically, a piezoelectric film is provided in front of the electromagnetic induction type shock-wave source. The shock-wave source is driven by a voltage lower than that for generating a shock-wave, so that a low-pressure wave lower in pressure than the shock-wave is sent to the interior of the body. The echoes of the low-pressure wave are received through the piezoelectric film. The intensity of each echo sent from the shock-wave focal zone, among all echoes, is detected. When the echo intensity is higher than a predetermined value, the drive voltage of the shock-wave source is switched to a high power, and a shock-wave for pulverizing a stone is emitted.

The following mechanism (means) is provided to achieve the second object of the present invention. More specifically, a shock-wave emitted from a first focal point of an underwater discharge type lithotrity apparatus having two focal points is reflected by a reflecting mirror, irradiates a stone positioned on a second focal point, and is received again by an ultrasonic probe or a sensor located at the first focal point through the reflecting mirror. Among the received echoes, the intensity of each echo sent from the focal zone is detected. When the echo intensity is higher than a predetermined value, a signal for designating discharge is sent to a discharge circuit by means of a triggering circuit determining a triggering timing and an ECG detecting circuit for obtaining synchronism with the cardiograph, and a shock-wave is emitted with a correct boresighting.

In order to achieve the third object, according to the present invention, the relation between the intensity of each echo detected in the above manner and the predetermined value is detected and determined by an echo intensity detecting circuit and a comparator (determining circuit). The intensity of the echo and the predetermined values can be informed to the operator as they are linked to each other. In fine, the apparatus of the present invention further has a means like this for informing a current state.

A shock-wave or a low-pressure wave emitted by the shock-wave source at the first focal point of the rotating elliptic reflecting mirror, or an ultrasonic wave emitted by an ultrasound probe, toward the interior of the patient's body, is reflected at different portions of the patient's body having different acoustic impedances.

In general, when a material, such as a stone, having a large acoustic impedance is present on the second focal point, a large echo is sent back. Hence, the degree of coincidence between the stone and the focal point can be detected in accordance with the intensity of the echo. On the other hand, when the stone is not present on the focal point but the focal point coincides with soft parts near a target, the intensity of the echo becomes extremely weak. Hence, e.g., with a shock-wave source using underwater discharge, if discharge is performed initially at a low voltage to generate a low-pressure wave, and if high-pressure discharge is performed when the echo intensity becomes higher than a predetermined value to emit a shock-wave, the shock-wave can radiate only the target (i.e., the stone). When the echo intensity and the predetermined value are informed to the operator by visual display and the like on a display screen as they are correlated with each other, they can be used as indices of correct positioning for boresighting.

When the intensity of the echo upon shock-wave radiation is compared with the predetermined value, it is also impossible to calculate the hit rate at which the shock-wave hits the stone.

In the predetermined region in front of the focal zone, e.g, the intensity of the echo sent from the patient's body surface does not become large if th coupling unit of the underwater discharge type lithotrity apparatus is in sufficient contact with the patient's body surface. However, if an amount of liquid in the coupling unit is not sufficient, or if an amount of coupling agent filled between the coupling unit and the body surface is not sufficient, an air layer exists midway along the propagation path of the low-pressure wave. Hence, the intensity of the echo from the body surface becomes undesirable large. Therefore, when the intensity of the echo is compared with the predetermined value, if the intensity of the echo is higher than the predetermined value, it is determined that the coupling unit and the patient's body surface are not in sufficient contact with each other, and this fact is informed to the operator as an alarm. When this alarm is performed, an unrequired radiation may not be performed to the interior of the patient, and thus radiation of a shock-wave not contributing to a lithotrity treatment (i.e., missed-shot) may not be performed. As a result, a reliable lithotrity treatment can be performed.

When an obstacle is present in front of a stone in the patient's body, the intensity of an echo reflected by this region becomes large. Hence, the presence of an obstacle can be detected by detecting the intensity of the echo. Then, it is possible to suggest to the operator that the direction of the shock-wave source be corrected, and the like.

Furthermore, the electromagnetic induction type shock-wave source is initially driven by a low voltage, and a weak low-pressure pulse wave not damaging a normal tissue in the patient's body is sent. The low-pressure wave supplied to the interior of the patient's body is reflected at different portions inside the body having different acoustic impedances. The echoes are received by a piezoelectric film arranged in front of the shock-wave source and only an echo signal component from, e.g., the shock-wave focal zone (to be abbreviated as "focal point" hereinafter) is extracted and its intensity is obtained.

When a material, such as a stone, having a large acoustic impedance is present on the focal point, a large echo is sent back. Hence, the matching degree of the stone and the focal point can be detected from the intensity of the echo. In contrast to this, when the stone is not present on the focal point and the focal point coincides with soft tissues, the echo becomes extremely weak. Therefore, when an echo intensity higher than a predetermined value is obtained, the drive voltage for the shock-wave source is increased to generate a shock-wave, thus enabling radiation of the shock-wave only onto the stone. When the echo intensity and the predetermined value are informed to the operator by monitor display or the like in a correlated manner, they can be used as indices of correct positioning.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1B is a block diagram of a lithotrity apparatus according to the second embodiment of the present invention;

DETAILED DESCRIPTION OF THE PREFERRED EMBODIMENTS

Figure 1A:
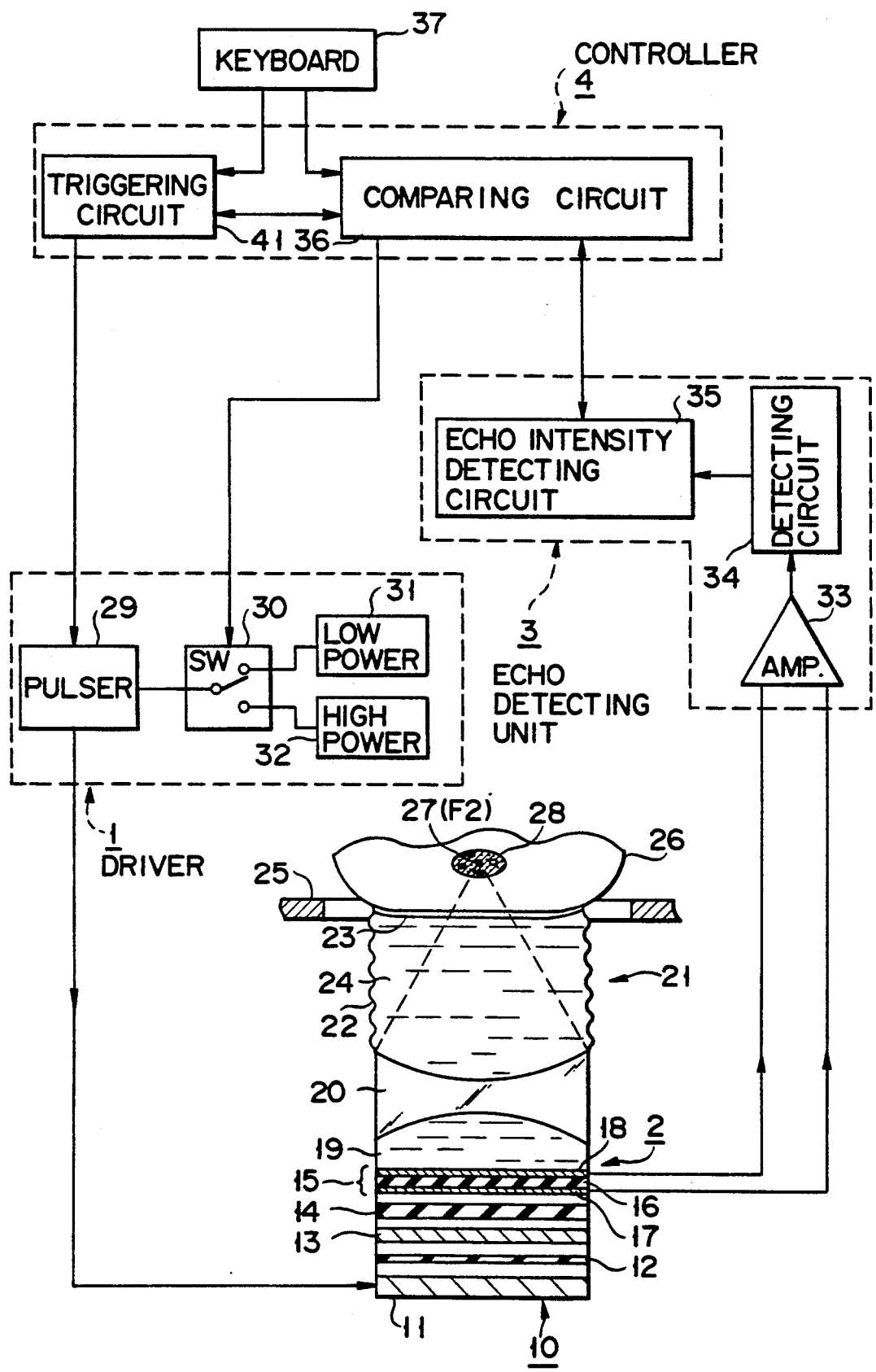
FIG. 1A is a block diagram of a lithotrity apparatus according to the first embodiment of th presēnt invention.

A lithotrity apparatus shown in FIG. 1A is one utilizing electromagnetic induction, which is the first embodiment of the present invention.

In an electromagnetic induction type shock-wave source 10, a coil 11 flatly wound in the same manner as the conventional case, an insulating sheet 12, and a conductive plate 13 are vertically, integrally stacked with considerably small gaps thereamong. An insulating sheet 14 and a piezoelectric film 15 are also vertically stacked with a small gap and are arranged in front of the shock-wave source 10. The piezoelectric film 15 is, e.g., a film obtained by forming electrodes 17 and 18 on the two surfaces of a piezoelectric layer 16, e.g., a PVDF film, by vapor deposition. The piezoelectric film 15 receives each echo from a patient, transduces the echo to an electric signal (RF signal), and outputs the electrical signal.

An acoustic lens 20 is arranged above the piezoelectric film 15 through water 19. A coupling unit 21 for coupling the shock-wave source 10 and a patient 26 is arranged above the acoustic lens 20. The coupling unit 21 comprises an extendable bag-like container constituted by a bellows 22, covering a portion in front of the acoustic lens 20, and a body surface contact film 23. Water 24 fills the container. As the body surface contact film 23, e.g., a rubber film is employed. When a treatment is performed, the body surface contact film 23 is brought into contact with the body surface of the patient 26 lying on a bed 25 through, e.g., a jellylike coupling agent.

The flat coil 11 is connected to a pulser 29. The pulser 29 is selectively connected to a low power supply 31 or a high power supply 32 by a switch 30 to generate a low- or high-voltage pulse. When a low-voltage pulse is applied to the coil 11 by the pulser 29, the electromagnetic induction type shock-wave source 10 generates a weak ultrasonic wave (low-pressure wave) (for boresighting); when a high-voltage pulse is applied, it generates a shock-wave (for stone pulverizing).

An RF signal output from the piezoelectric film 1 is input to an amplifier 33. The amplifier 33 amplifies the RF signal and supplies the amplified signal to a detecting circuit 34. The detecting circuit 34 detects the output from the amplifier 33 and converts it to a unipolar signal. An echo intensity detecting circuit 35 detects the intensity (e.g., a peak value) of the echo from the output signal of the detecting circuit 34.

A controller 4 supplies trigger pulses to the pulser 29 at predetermined intervals based on an instruction input through a keyboard 37, and a switching signal to the switch 30. A comparing circuit 36 also controls the echo intensity detecting circuit 35 and compares an echo intensity to be described later with a predetermined value.

The operation of this embodiment will be described with reference to the timing charts of FIGS. 2A and 2B.

The switch 30 is controlled by the comparing circuit 36 and performs a switching operation. At the start of a lithotrity treatment, the switch 30 connects the pulser 29 to the low power supply 31, as shown in FIG. 1A. Thus, when the pulser is activated by a trigger pulse from a triggering circuit 41, it generates a low-voltage pulse first. When this low-voltage pulse is applied to the flat coil 11, a weak repulsive force is generated in the conductive plate 13 accordingly, and a weak plane wave (low-pressure wave) is radiated into water 19 contacting the conductive plate 13. The insulating sheet 14 and the piezoelectric film 15 are sufficiently thin. Therefore, when the low-voltage wave is transmitted through the sheet 14 and the film 15 without substantially being attenuated, it then passes through the water 24 inside the coupling unit 21 and the body surface contact film 23 through the acoustic lens 20, and is focused on a focal point 27 located inside the body of the patient 26. At this time, the pressure of the low-pressure wave at the focal point 27 is sufficiently small so as not to damage a normal tissue. The low-pressure wave is reflected at the respective portions inside the body of the patient 26 and is transmitted through the same path as the incident path. This echo as the reflected wave is converted into a plane wave through the acoustic lens 20, is incident on the piezoelectric film 15, and is derived as an RF signal. The RF signal is amplified by the amplifier 33 and is detected by the detecting circuit 34.

Figure 2A:
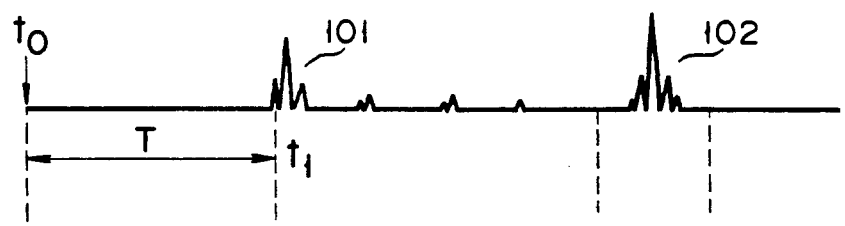
FIG. 2A is a signal waveform chart showing an echo with an apparatus of the present invention.

The waveform chart shown in FIG. 2A shows the waveform of the echo signal detected by the detecting circuit 34. Reference symbol to denotes a time point when the low-pressure wave was emitted, and reference numeral 101 denotes the waveform of the echo reflected by the body surface of the patient 26. Although the water 19, the acoustic lens 20, the water 24 inside the coupling unit 21, and the body surface contact film 23 are present between the piezoelectric film 15 and the body surface of the patient 26, a reflecting phenomenon can be ignored. Therefore, no echo signal can substantially appear between the time point t0 and the generation of the body surface echo signal 101.

Upon reception of an output from the echo intensity detecting circuit 35, the comparing circuit 36 detects a time T between the time point t0 and the generation of the body surface echo signal waveform 101 of FIG. 2A, thereby detecting a time point t1 when the body surface echo starts to be received. This can be realized by detection of a first peak (i.e., 101) in accordance with a known technique. It is also possible to set a shot designating (trigger) timing for lithotrity by utilizing the signal detected by the piezoelectric film 15 which is obtained when the low-pressure wave emitted by the shock-wave source 10 passes through it.

A controller 4 controls the entire apparatus in accordance with the designation made by the operator input through the keyboard 37 and comprises the comparing circuit 36 and the triggering circuit 41. After the designation for the shot timing control as described above, the comparing circuit 36 supplies a focal zone echo gate 104 that lasts for a period $\tau_2$ to the echo intensity detecting circuit 35 which contains an echo signal 102 (refer to FIG. 2A) sent from the vicinity of the focal point 27 (focal zone). In this case, the focal zone echo gate 104 may be set after the trigger timing (t0) of the pulser 29 and after a time required for the shock-wave to reciprocate the distance to the focal point 27. It is obviously possible to set the trigger timing by utilizing the signal detected from the piezoelectric film 15 when the low-pressure wave emitted by the shock-wave source 10 passes through it, as described before. Hence, the echo intensity detecting circuit 35 consecutively detects the echo peak value within the period $\tau_2$ and sends the detected value to the controller 4 (36).

The controller 4 (36) compares the peak value of the echo sent from the focal zone and detected in this sequence with a second predetermined value $TH_2$ input through the keyboard 37. When the peak value of the echo is higher than the predetermined value $TH_2$, the controller 4 (36) determines that a stone 28 is located at the position of the focal point 27 and supplies a switching signal to the switch 30 so that the pulser 29 is switched to the high power supply 32 side. Therefore, upon reception of a trigger pulse from the controller 4 (36), the pulser 29 generates a high-voltage pulse. A shock-wave is generated by the electromagnetic induction type shock-wave source 10 to the focal point 27 by this high-voltage pulse and correctly irradiates the stone 28 located on the focal point 27. Conversely, when the peak value of the echo sent from the focal zone is smaller than the second predetermined value $TH_2$, it is determined that the stone 28 is not located on the focal point 27. Therefore, the switch 30 is maintained to be connected to the low power supply 31 side. As a result, the shock-wave source 10 keeps emitting a low-voltage wave for stone search.

FIG. 1B shows a lithotrity apparatus according to the second embodiment of the present invention. In addition to the arrangement shown in FIG. 1A, this apparatus has a CRT display 38 and an alarm unit 39 connected to the controller 4 (36). By the control of the controller 4 (36), the peak value of the echo sent from the focal zone and detected by the echo intensity detecting circuit 35 is displayed on the CRT display 38 together with the second predetermined value $TH_2$. The operator can easily perform alignment of the focal point 27 with the stone 28 or adjusting the value $TH_2$ at an optimum value by referring to these data as indices.

Figure 4A:
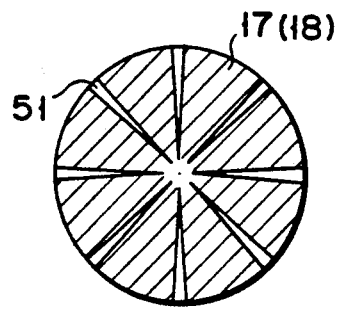
FIGS. 4A and 4B are plan views showing the electrode shapes of a piezoelectric film of an apparatus of the present invention.
Figure 4B:
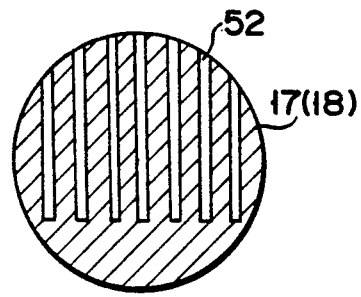

In the two embodiments above, the shape of the electrodes 17 and 18 of the piezoelectric film 15 is not described. In the embodiments, the entire surface of the piezoelectric film 15 is uniform. However, a piezoelectric film having a shape as shown in FIG. 4A or 4B can also be used. More specifically, FIG. 4A shows an example of a piezoelectric film in which radial slits 51 are formed in the electrode 17 (18). FIG. 4B shows an example of a piezoelectric film in which a plurality of parallel slits 52 are formed in the electrode 17 (18). When such slits 51 or 52 are formed, the conductivity of the electrodes 17 and 18 in the radial direction is decreased, so that an eddy current generated within the electrodes by a pulse magnetic field, generated when an intense shock-wave is irradiated, is reduced. As a result, the stress applied to the piezoelectric film 15 can be minimized. When this improvement is done, the mechanical service life of the piezoelectric film 15 can be prolonged.

Figure 1C:
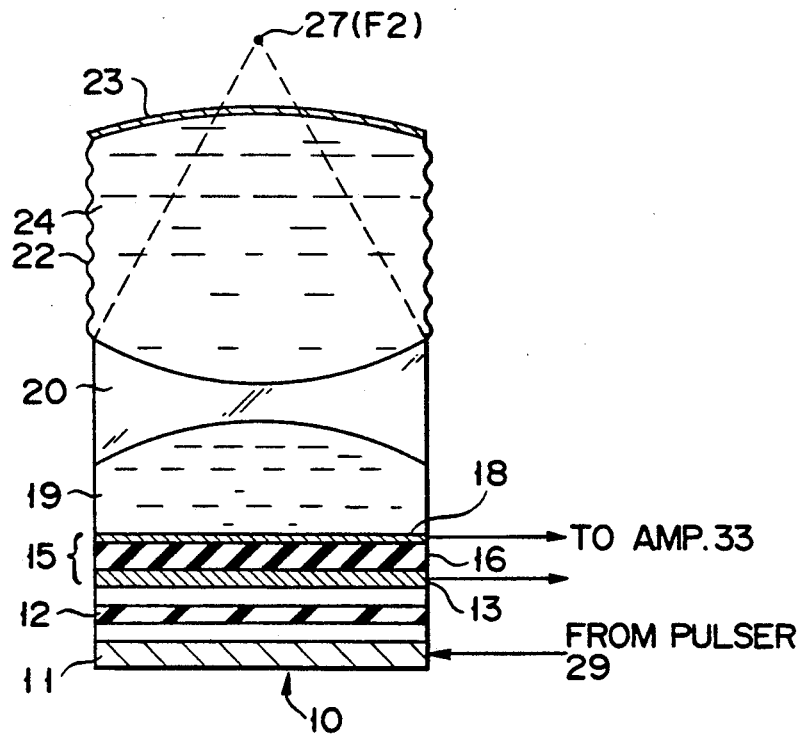
FIG. 1C shows the arrangement of a main part of a lithotrity apparatus according to the third embodiment of the present invention.
Figure 6:
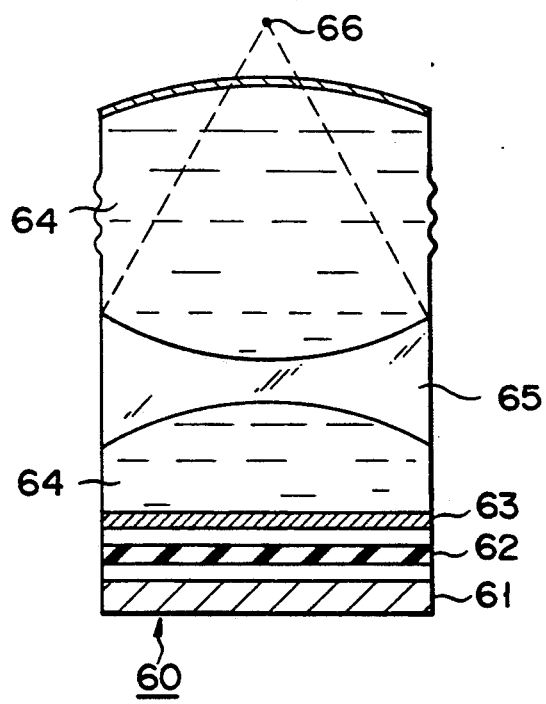
FIG. 6 shows the arrangement of a main part of a conventional lithotrity apparatus.

In the first and second embodiments, the insulating sheet 14 and the piezoelectric film 15 for the purpose of echo detection are added to the electromagnetic induction type shock-wave source 10 having the same arrangement as that of a conventional apparatus. However, as in the third embodiment shown in FIG. 1C, the piezoelectric film 15 can be integrally formed with the conductive plate 13 so that the insulating sheet 14 can be omitted. In other words, in FIG. 1C, one electrode of the piezoelectric film 15 may be adhered to the conductive plate 13 to be electrically conductive. As a result, one electrode of the piezoelectric film 15 and the conductive plate 13 are commonly used.

In the above embodiments, the CRT display 38 is used as a means to send data to the operator. However, if an ultrasonic diagnosing apparatus can be used for "positioning", an ultrasonic image such as a B mode sector image 30, shown in FIGS. 3A to 3C, can be displayed simultaneously on the same CRT display 38, so that the operator can visually recognize both the echo intensity and the image simultaneously and totally without a time lag. As a result, "positioning" for a lithotrity treatment is facilitated.

As the display means of the echo intensity, a level meter using light-emitting diodes can be used in place of the CRT display 38. The echo intensity can be expressed by way of a sound intensity or a tone change.

In the first to third embodiments, two types of power units, i,e., the low power supply 31 and the high power supply 32 are prepared for supplying power to the pulser 29, and these units are switched by the switch 30. However, the same effect can be obtained even if only one power source is prepared and its voltage level is changed as required.

Since the piezoelectric film is arranged i front of the electromagnetic induction type shock-wave source, the echo intensity is detected, thereby controlling radiation of the shock-wave in accordance with the magnitude of a predetermined value.

Figure 5A:
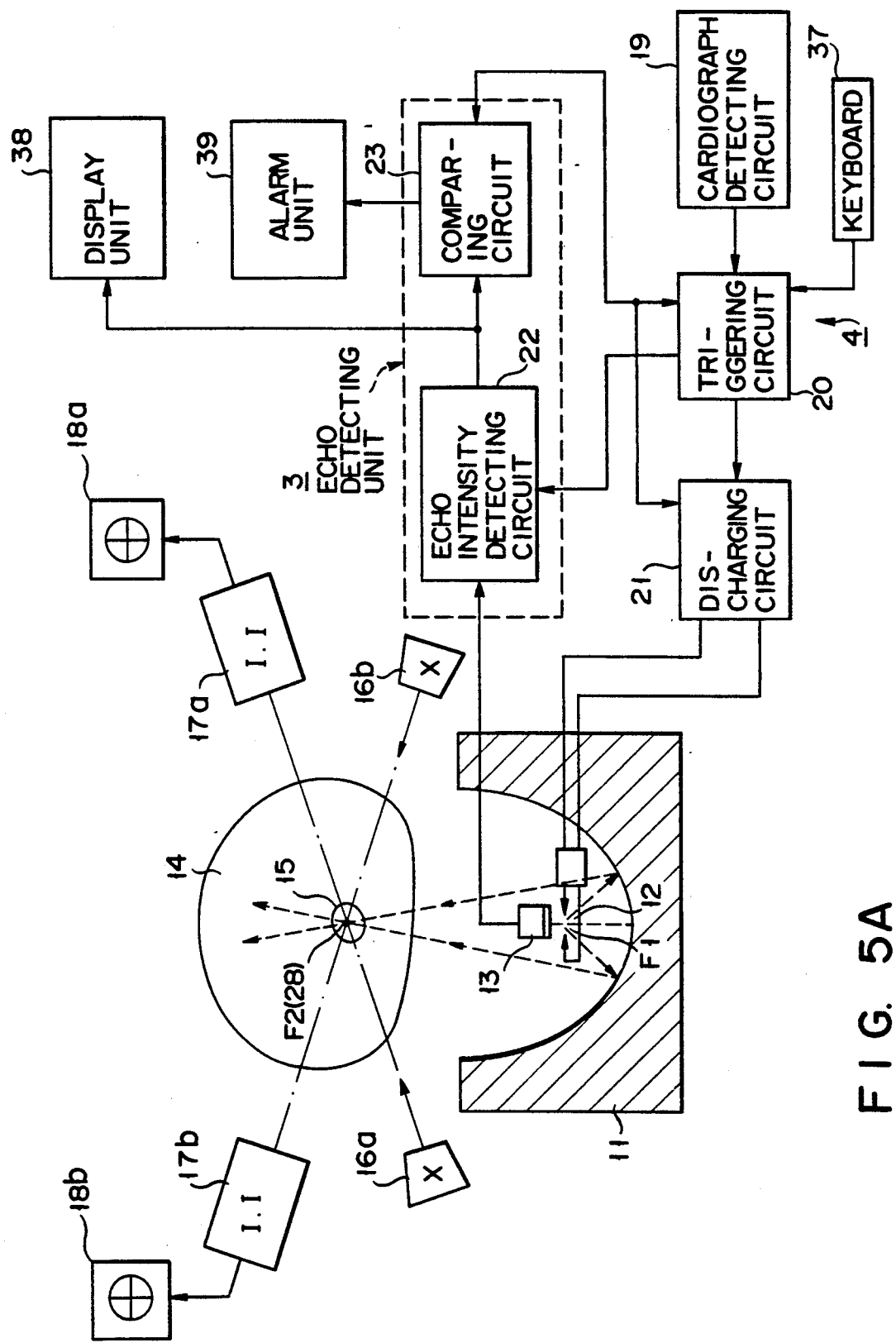
FIG. 5A is a block diagram of an underwater discharge type lithotrity apparatus according to the fourth embodiment of the present invention.

FIG. 5A shows an underwater discharge type lithotrity apparatus according to the fourth embodiment of the present invention. Referring to FIG. 5A, a rotating elliptic reflecting mirror 11 has two focal points F1 and F2. A discharge gap 12 as a shock-wave source is arranged at the first focal point F1, and a sensor 13 is arranged at a position in front of the discharge gap 12 on the side of the second focal point F2.

A stone 15 inside the body of a patient 14 is localized at the second focal point F2 of the rotating elliptic reflecting mirror 11. Localization is performed by X-ray fluoroscopy in two directions. More specifically, a stone image is detected by the operation of X-ray tubes 16a and 16b and corresponding image intensifiers 17a and 17b. The patient 14 is moved to a position where its stone images are formed on the focal points on monitor units 18a and 18b.

When the operator depresses a start key on a keyboard 37, radiation designation for lithotrity treatment is started. The radiation timing of an actual shock-wave is synchronized with the cardiograph. A cardiograph detecting circuit 19 detects the cardiograph of the patient 14 by electrodes (not shown). A signal detected by the cardiograph detecting circuit 19 is supplied to a triggering circuit 20 to generate a discharge trigger signal. The discharge trigger signal is sent to a discharging circuit 21, and a shock-wave is generated at a moment when discharge is performed through the discharge gap located at the focal point F1.

A sensor 13 located in the vicinity of the focal point F1 detects the direct wave of the shock-wave generated by the discharge gap 12 and its echoes sent from inside the body, and outputs the detection result to an echo intensity detecting circuit 22 as an electrical signal. As the sensor 13 made from a piezoelectric material, e.g., piezo-ceramic, quartz, and PVDF (Poly-Vinyli-Dene Fluoride), a semiconductor distortion sensor, or the like is used. A protection plate for echo attenuation may be placed, depending on the types of the sensor 13, between the discharge gap 12 and the sensor 13.

When a shock-wave is emitted by the discharge gap 12, its direct wave is first detected by the sensor 13. The shock-wave is reflected by the rotating elliptic reflecting mirror 11 and irradiates the stone 15 located at the second focal point F2. The shock-wave is reflected by the stone 15. The echoes returned to incident on the first focal point F1 of the rotating elliptic reflecting mirror 11 are detected by the sensor 13, converted into an electrical signal (RF signal), and is output. The output signal from the sensor 13 is input to the echo intensity detecting circuit 22. The echo intensity detecting circuit 22 is subjected to sampling gate by a signal from the triggering circuit 20 for a time period during which the echo from the focal zone is detected. An echo intensity during this sampling gate, i.e., the echo intensity from the stone is detected. The echo intensity detected by the detecting circuit 22 is visually displayed on, e.g., the display unit 38 using a CRT, as shown in FIG. 5A.

In general, since a stone in a body has a higher acoustic impedance than a normal soft tissue around it, it emits echoes of a high intensity. Therefore, when the stone 15 is located at the second focal point F2 of the rotating elliptic reflecting mirror 11, a high-intensity echo can be obtained. On the contrary, when the stone 15 is located off the focal point F2, substantially no echo is obtained.

Another type of a lithotrity apparatus which does not detect an echo of an intense shock-wave, as described above, is also possible. For example, a discharging circuit 21 may be operated by a discharge voltage lower than that used for generating a shock-wave for lithotrity, so that a discharge gap 12 performs a weak discharge. The echo of the shock-wave is then detected by a sensor 13. In this case, the echo intensity detected by an echo intensity detecting circuit 22 is compared with a predetermined value by a comparing circuit 23. When the echo intensity is higher than the predetermined value, it is determined that a stone 15 is located at the second focal point F2. The discharge trigger signal from the triggering circuit 20 is controlled to switch the discharge voltage to a high voltage. Then, a shock-wave for lithotrity is emitted. When the discharge gap 12 is to be discharged at a low voltage, its preset voltage may be controlled. An inter-electrode distance (gap length) forming the discharge gap 12 may be changed, or a special electrode for low voltage may be provided.

The graph of FIG. 2A is a signal waveform chart indicating an echo when the apparatus of this embodiment is used. The waveform is that of the echo signal detected by the sensor 13 of FIG. 5A. In FIG. 2A, reference symbol t0 denotes a time point when the discharge gap 12 emits a shock-wave or a low-pressure wave. Reference numeral 101 denotes an echo signal sent from the body surface, and 102, an echo signal from a zone including the focal point F2. The intensity of the echo signal (waveform) sent from the body surface is increased when the contacting state between a coupling unit (portion filled with water) (not shown), provided between the rotating elliptic reflecting mirror 11 and the patient 14, and the patient 14 is not good. In this case, the contacting state with the body surface can be obtained in the following manner.

A time T from t0 till a time point when the body surface echo signal 101 is detected in FIG. 2A is detected by a controller not shown, thereby detecting a body surface echo reception start time point t1. This is realized by a known technique to detect a first peak (101). A body surface echo gate 103 is set by the controller to correspond to a period of time $\tau_1$ before and after the time point t1, as shown in FIG. 2B. This body surface echo gate 103 is set in the echo intensity detecting circuit 22. Thus, the echo intensity detecting circuit 22 detects, e.g., a peak value of the echo signal (to be referred to as an echo peak value hereinafter) during the period $\tau_1$. The comparing circuit 23 compares the echo peak value with a first predetermined value (threshold value $TH_1$). When the echo peak value is smaller than the predetermined value $TH_1$, no measure is taken. When the echo peak value is higher than the predetermined value $TH_1$, it is determined that the contact between the patient 14 and the coupling unit is not sufficient. The alarm unit 24 using a buzzer or a lamp, or both, is caused to perform an alarm operation, and this determination result is informed to the operator. As a result, the operator can know that the water amount in the coupling unit is not sufficient, or that the amount of the coupling agent (e.g., jelly) between the coupling unit and the body surface is not sufficient.

Figure 2B:
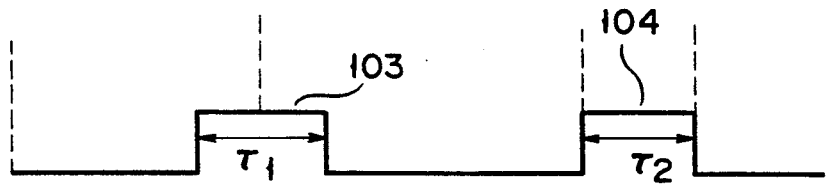
FIG. 2B is a timing chart of echoes when measurement is performed with an apparatus of the present invention.

After this control as described above, a focal zone wave gate 104 is set to last for a period of time $\tau_2$ including the echo signal 102 sent from the nearby zone (focal zone) of the focal point F2 in FIG. 5A by the controller in accordance with the timing chart of the echo gate shown in FIG. 2B. This focal zone wave gate 104 is set in the echo intensity detecting circuit 22 The focal zone echo gate 104 may be set after a time required for reciprocating the distance to the focal point F2 after the trigger timing (t0) of the triggering circuit 20. It is also possible to detect by the sensor 13 the low-pressure direct wave emitted by the discharge gap 12, thereby obtaining a radiation timing. In this way, the echo intensity detecting circuit 22 detects this time the echo peak value within the period $\tau_2$. The comparing circuit 23 compares the echo peak value sent from the focal zone and detected in accordance with the procedures described above, with a second predetermined value (to be referred to as threshold value $TH_2$). When the echo peak value is the predetermined value $TH_2$ or higher, the comparing circuit 23 determines that the stone 15 coincides with the focal point F2 and controls the triggering circuit 20 to switch the discharge voltage to a high voltage, thereby generating the shock-wave by the discharge gap 12. The shock-wave correctly irradiates the stone 15 located at the focal point F2. On the contrary, when the echo peak value sent from the focal zone is smaller than the second predetermined valve $TH_2$, it is determined that the stone 15 is not located at the focal point F2. Thus, the discharge voltage is kept low, and the discharge gap 22 keeps emitting a low-pressure wave for stone search.

A display unit 38 and an alarm unit 39 ar also provided. More specifically, the alarm unit 39 comprises an alarm system such as a buzzer, and the display unit 38 comprises a graphic display or a CRT. The location of the stone 15 and that of the focal point F2 are visually informed to the operator by means of the display unit 38 connected to the echo intensity detecting circuit 22. When the boresight before lithotrity radiation is off the target, this fact can be informed by the alarm unit 39 using the buzzer. In this manner, when data concerning the boresighting state and irradiating state are sequentially informed to the operator, the usability of the lithotrity apparatus is improved.

The display unit 38 is controlled by the controller to display, together with the second predetermined value $TH_2$, the echo peak value sent from the focal zone and detected by the echo intensity detecting circuit 22. By using the displayed echo peak value and the second predetermined value $TH_2$ as the indices, the operator can localize the focal point F2 with the stone 15, or adjust the predetermined value $TH_2$ at an optimum value.

Figure 3A:
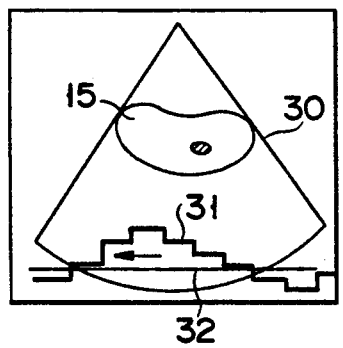
FIGS. 3A to 3C show examples of display layouts of an apparatus of the present invention.
Figure 3B:
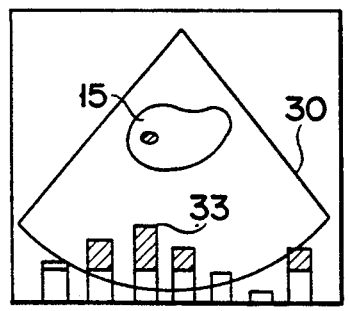
Figure 3C:
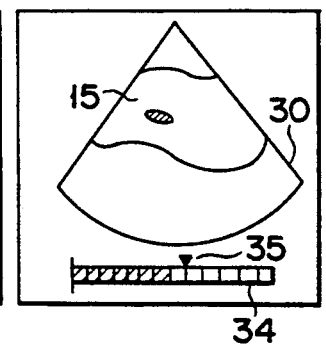

FIGS. 3A to 3C show typical display examples by the display unit 38. FIG. 3A shows a screen layout of a trend graph 31 which successively indicates echo peak values, sent from the focal zone and varying as the time passes, in the viewfield of a B mode sector image 30 indicating a diseased part inside the patient's body which is obtained by an ultrasonic probe (not shown). The predetermined value $TH_2$ is designated by means of a keyboard or the like by the operator and displayed by way of a line 32 on the display screen. The trend graph 31 changes as time passes and is moved in the direction of an arrow.

FIG. 3B is an example of a screen layout in which the echo peak value as that described above is displayed by way of a histogram. The echo peak value that varies along with time is displayed on the viewfield of the B mode sector image 30 indicating the diseased part (stone) 15 of the patient's body. This histogram 33 also changes as time passes and is moved in the direction of an arrow. A value equal to or larger than the predetermined value $TH_2$ is displayed with a different tone or brightness value different from that of a value less than the predetermined value $TH_2$. Therefore, it is easy to decide which is higher, the predetermined value $TH_2$ or the echo peak value.

When time-base recording is not necessary, a simpler screen layout as shown in FIG. 3C may be adopted. In this case, other than a focal zone that varies as a function of time, only a single level meter 34 and a mark 35 indicating the predetermined value $TH_2$ are displayed in viewfield of a B mode sector image 30 representing the diseased part 15 inside the patient's body.

The operator boresights the stone of the diseased part as he selectively switches the display screens described above as necessary. Then, the operator designates start of a pulverizing operation to the apparatus by depressing a start bottom of a keyboard or the like. In this manner, when the screen surfaces of the display unit described above are used, a lithotrity treatment is simplified, and a missed-shot to a normal tissue other than a target stone is prevented.

A rib, a lung, intestinal gas, and the like are known as obstacles to interfere with propagation of a shock-wave on the stone 15. In order to improve lithotrity efficiency and to decrease a side-effect, it is important to select an incident path so as to avoid reflection of the shock-wave by such an obstacle. The presence of such an obstacle ca be detected in the following manner. A low-pressure wave is emitted by the discharge gap 12, and its echoes are received and detected by the sensor 13. A peak value of an echo sent from an internal obstacle such as a rib or a lung present between the body surface and the focal zone is detected, and the detected value is compared with a third predetermined value (threshold value $TH_3$). When the echo peak value is equal to or smaller than, e.g., the predetermined value $TH_3$, no problem is posed. However, when the echo peak value is larger than the predetermined value $TH_3$, it is determined that a large obstacle is present on the propagation path of the echo. Hence, it is preferable that this fact is informed to the operator by means of the alarm unit 39, such as a buzzer or a lamp, or the display unit 38. Upon recognition of the alarm, the operator adjusts the position and direction of the applicator, i.e., the shock-wave source, and the coupling unit so that the obstacle becomes off the propagation path of the shock-wave. When the apparatus main body has a function to move the applicator, the data from the controller may be fed back to this mechanism and automatic position adjustment may be performed so that the obstacle on the incident path of the shock-wave is reduced. With this mechanism, automatic lithotrity treatment is realized.

Figure 5B:
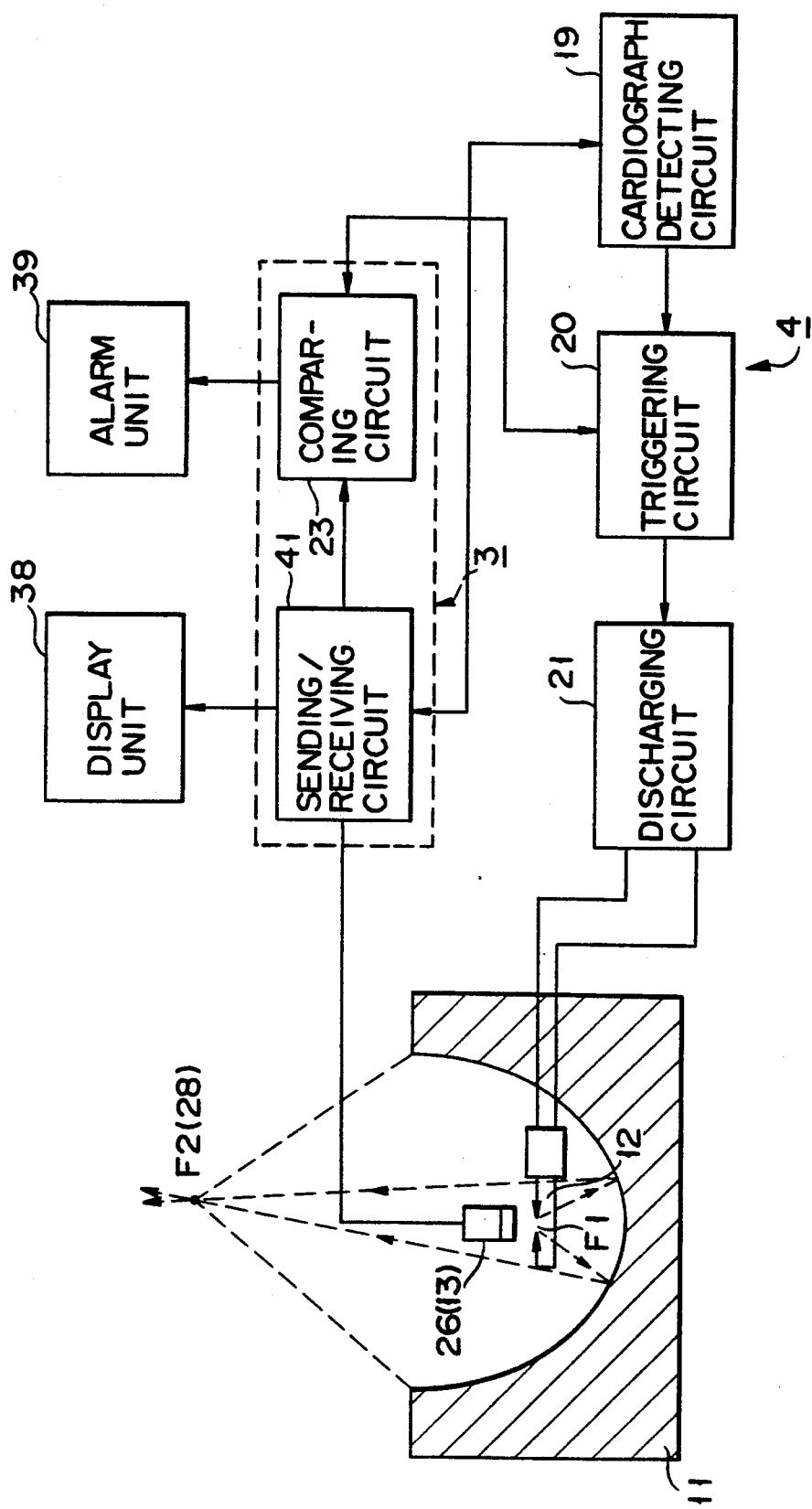
FIG. 5B is a block diagram of an underwater discharge type lithotrity apparatus according to the fifth embodiment of the present invention.

FIG. 5B shows the arrangement of a lithotrity apparatus according to the fifth embodiment of the present invention. This embodiment is different from the fourth embodiment in that an ultrasonic probe 26 is employed in place of the sensor 13 in FIG. 5A The ultrasonic probe 26 is connected to a sending/receiving circuit 41. The sending/receiving circuit 41 receives a signal from a cardiograph detecting circuit 19 and pulse-drives the ultrasonic probe 26 to be synchronous with the signal reception. With this mechanism, the ultrasonic probe 26 emits an ultrasonic pulse. The emitted pulse is reflected by a rotating elliptic reflecting mirror 11 and is focused on a second focal point F2. The pulse is then reflected by a stone set at the second focal point F2. The echo signal returning through the reflecting mirror 11 is detected and output as an electrical signal (echo signal). The echo signal is compared with various predetermined values by a comparing circuit 23 in accordance with a mechanism similar to those of the embodiments described above. A control similar to those of the embodiments described above is performed based on the comparison result.

In the present invention, echo signals sent from various zones, such as a patient's body surface or a focal zone, are subjected to a sampling gate (103, 104) in order to detect the echo intensities. A peak value of an echo during this gate period is detected (calculated). An integral of an echo signal during an appropriate sampling gate may be calculated in order to decrease the adverse effect caused by interference of the echo. When this integration method is used, it is effective to multiply the echo signal by a weighting function according to a depth direction and thereafter integrate the product, rather than to simply integrate the echo signal during the sampling gate.

In the present invention, the applicator (i.e., the main part of the lithotrity mechanism) is arranged under the patient. However, it can be arranged above the patient.

As a display means of an echo intensity, a level meter using a light-emitting diode can also be used in place of the display unit 38 using a CRT.

An echo intensity may be informed by way of different sound volumes obtained by modulating an audible sound. A displacement of a stone from a focal point may be informed by way of a message (e.g. an alarm) obtained by sound synthesis.

It is also effective to count the number of shock-waves hitting a stone during a lithotrity treatment, and to output the count to the display unit as a hit rate.

In the present invention, the lithotrity apparatus utilizes underwater discharge as a shock-wave source. However, a small explosion of a small amount of an explosive may be utilized as the shock-wave source.

Various changes and modifications may be made within the spirit and scope without departing from the invention.

As has been described above, according to the present invention, a sensor or an ultrasonic probe is arranged in the vicinity of a first focal point of a rotating elliptic reflecting mirror, to which a shock-wave source is provided, to detect an echo intensity. The echo signal intensity is compared with a predetermined value, and radiation of the shock-wave is controlled in accordance with the comparison result. When the comparison result of the echo intensity and the predetermined value is informed to the operator, the operator can easily and correctly irradiate only a stone to be pulverized with the shock-wave. As a result, a missed-shot to a normal tissue is prevented, thus providing a lithotrity apparatus having a high lithotrity efficiency with small side-effect to a human body.

According to the present invention, a mechanism is provided to inform that the intensity of an echo sent from the body surface or internal obstacle of a patient becomes equal to or higher than a predetermined value. With this mechanism, the contacting state of the patient and the coupling unit is informed to the operator. It is also possible to suggest to the operator that the location or direction of the applicator be changed so that the shock-wave may be irradiated to avoid an internal obstacle.

When the sensor or the ultrasonic probe is arranged immediately before the shock-wave source, the shock-wave emitted by the shock-wave source and directly irradiating a zone of the rotating elliptic reflecting mirror outside a region including the second focal point may be decreased. As a result, discomfort of the patient during treatment can be decreased.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A lithotrity apparatus, comprising:
   a shock-wave source for generating a shock-wave;
   focusing means to focus the shock-wave at a predetermined position, for focusing and irradiating the shock-wave toward a stone in a body of a patient which is located at the predetermined position, thereby pulverizing the stone;
   drive means for driving said shock-wave source by a voltage lower than that for generating the shock-wave so as to send a low-pressure wave lower in pressure than the shock-wave to the inside of the body;
   echo receiving means arranged in front of said shock-wave source, for receiving a low-pressure echo reflected from the body;
   echo detecting means for detecting the intensity of an echo received by said echo receiving means, reflected by a focal zone of the shock-wave; and
   control means for comparing the intensity of the echo detected by said echo detecting means with a predetermined value, sending a predetermined signal to said drive means based on the comparison result, switching the drive voltage of said shock-wave source to a high voltage sufficient for lithotrity, and generating a signal for driving said shock-wave source;
   wherein said echo receiving means comprises a piezoelectric film arranged in front of said shock-wave source, said piezoelectric film comprising:
   a piezoelectric layer made of a PVDF (Poly-Vinyli-Dene-Fluoride) film;
   an electrode formed on a first surface of said piezoelectric layer by vapor deposition; and
   a conductive plate formed on a second surface of said piezoelectric layer so as to be electrically conductive with said electrode;
   wherein the echo is received and converted into an electrical signal, and the electrical signal is sent to said echo detecting means;
   said electrode formed on the first surface of said piezoelectric film having a plurality of slits each having a predetermined width.

2. A lithotrity apparatus, comprising:
   a shock-wave source for generating a shock-wave;
   focusing means to focus the shock-wave at a predetermined position, for focusing and irradiation the shock-wave toward a stone in a body of a patient which is located at the predetermined position, thereby pulverizing the stone;
   drive means for driving said shock-wave source by a voltage lower than that for generating the shock-wave so as to send a low-pressure wave lower in pressure than the shock-wave to the inside of the body;
   echo receiving means arranged in front of said shock-wave source, for receiving a low-pressure echo reflected from the body;
   echo detecting means for detecting the intensity of an echo received by said echo receiving means, reflected by a focal zone of the shock-wave; and
   control means for comparing the intensity of the echo detected by said echo detecting means with a predetermined value, sending a predetermined signal to said drive means based on the comparison result, switching the drive voltage of said shock-wave source to a high voltage sufficient for lithotrity, and generating a signal for driving said shock-wave source;

wherein said echo receiving means comprises a piezoelectric film arranged in front of said shock-wave source, said piezoelectric film comprising:

a piezoelectric layer made of a PVDF (Poly-Vinyli-Dene-Fluoride) film;

an electrode formed on a first surface of said piezoelectric layer by vapor deposition; and a conductive plate formed on a second surface of said piezoelectric layer so as to be electrically conductive with said electrode;

wherein the echo is received and converted into an electrical signal, and the electrical signal is sent to said echo detecting means;

said electrode formed on the first surface of said piezoelectric film having a plurality of slits each having a predetermined width; and each of said slits is a radial slit extending to a center of the surface of said electrode.

3. A lithotrity apparatus, comprising:

a shock-wave source for generating a shock-wave;

focusing means to focus the shock-wave at a predetermined position, for focusing and irradiating the shock-wave toward a stone in a body of a patient which is located at the predetermined position, thereby pulverizing the stone;

drive means for driving said shock-wave source by a voltage lower than that for generating the shock-wave so as to send a low-pressure wave lower in pressure than the shock-wave to the inside of the body;

echo receiving means arranged in front of said shock-wave source, for receiving a low-pressure echo reflected from the body;

echo detecting means for detecting the intensity of an echo received by said echo receiving means, reflected by a focal zone of the shock-wave; and control means for comparing the intensity of the echo detected by said echo detecting means with a predetermined value, sending a predetermined signal to said drive means based on the comparison result, switching the drive voltage of said shock-wave source to a high voltage sufficient for lithotrity, and generating a signal for driving said shock-wave source;

wherein said echo receiving means comprises a piezoelectric film arranged in front of said shock-wave source, said piezoelectric film comprising:

a piezoelectric layer made of a PVDF (Poly-Vinyli-Dene-Fluoride) film;

an electrode formed on a first surface of said piezoelectric layer by vapor deposition; and a conductive plate formed on a second surface of said piezoelectric layer so as to be electrically conductive with said electrode;

wherein the echo is received and converted into an electrical signal, and the electrical signal is sent to said echo detecting means;

said electrode formed on the first surface of said piezoelectric film having a plurality of slits each having a predetermined width; and each of said slits being a parallel slit extending in a predetermined direction and having a predetermined width.

* * * * *